US00RE40835E

(19) United States
(12) Reissued Patent
Shi et al.

(10) Patent Number: US RE40,835 E
(45) Date of Reissued Patent: Jul. 7, 2009

(54) ENHANCEMENT OF IMMUNOCHEMICAL STAINING IN ALDEHYDE-FIXED TISSUE

(75) Inventors: Shan-Rong Shi, Los Angeles, CA (US); Atul K. Tandon, Fremont, CA (US); Krishan L. Kalra, Danville, CA (US); Nagesh Malhotra, Los Angeles, CA (US); Sheng-Hui Su, San Ramon, CA (US); Cheng-Zhi Yu, Pleasant Hill, CA (US)

(73) Assignee: BioGenx Laboratories, Inc., San Ramon, CA (US)

(21) Appl. No.: 11/249,180

(22) PCT Filed: Aug. 12, 1993

(86) PCT No.: PCT/US93/07550

§ 371 (c)(1),
(2), (4) Date: Apr. 7, 1994

(87) PCT Pub. No.: WO94/04906

PCT Pub. Date: Mar. 3, 1994

Related U.S. Patent Documents

Reissue of:
(64) Patent No.: 5,578,452
Issued: Nov. 26, 1996
Appl. No.: 11/249,180
Filed: Oct. 11, 2005

U.S. Applications:
(63) Continuation-in-part of application No. 07/928,962, filed on Aug. 12, 1992, now abandoned, which is a continuation-in-part of application No. 07/821,931, filed on Jan. 16, 1992, now abandoned.

(51) Int. Cl.
*G01N 33/567* (2006.01)

(52) U.S. Cl. ..... 435/7.21; 435/7.95; 435/40; 435/52; 436/63; 436/175

(58) Field of Classification Search ..... 435/7.21, 435/7.95, 40, 52; 436/63, 175, 518, 525
See application file for complete search history.

(56) References Cited

U.S. PATENT DOCUMENTS 4,910,132 A * 3/1990 Knight et al. ..... 435/5
4,921,841 A * 5/1990 Obrig ..... 514/8
5,188,834 A 2/1993 Grimm et al.
5,242,828 A * 9/1993 Bergstrom et al. ..... 435/287.1
5,451,527 A * 9/1995 Sarin et al. ..... 436/518
5,705,649 A * 1/1998 Shultz et al. ..... 548/126

OTHER PUBLICATIONS

Ed Harlow and David Lane; Antibodies: a laboratory manual, Cold Spring Harbor Laboratory 1988, pp. 316–318.*
P Rumph et al., Anat. Histol. Embryol., vol. 15, No. 3, pp. 269–276 (1986).
P. Rumph et al. Anat. Histol. Embryol., vol. 17, No. 3, pp. 226–231 (1988).
A. Ross, J. Electron Microsc. Tech., vol. 5, No. 1, pp. 81–90 (1987).
E. Gendler, English Abstract of U.S.S.R. Patent No. 138,336 (1960).
K. Yasuda, HCAPLUS Abstract of Saibo, vol. 15, No. 4, pp. 545–547 (1983).
N. Yamamoto et al. HCAPLUS Abstract of Kitasato Igaku, vol. 11, No. 1, pp. 9–17 (1981).
Harlan and Feairheller, "Chemistry of the CrossLinking of Collagen During Tanning", Adv Exp Med Biol (1977) 86A:425–440.
Kelly, et al., "Cross–Linking of Amino Acids By Formaldehyde Preparation and Carbon–13 NMR Spectra of Model Compounds", Adv Exp Med Biol (1977) 86A:641–647.
Fraenkel–Conrat, et al., (1947) "The Reaction of Formaldehyde with Proteins (IV) Participation of Indole Groups. Gramicidin" J. Biol. Chem., 168:99–118.
Fox, (1985) J. Histochem. Cytochem. 33:845–855.
Jones, (1973) "Reactions of aldehyde with unsaturated fatty acids during histological fixation" Fixation in Histochemistry, P. J. Stoward, ed.
Kunkel et al., (1981) Mol. Cell. Biochem. 34:3.
March, (1968) "Advanced Organic Chemistry," particularly at 333, 424, 670–672.
Mayers, J. Clin. Pathol. (1970) 28:273.
Hopwood et al., Histochem. J. (1984) 16:1171.
Battifora and Kopinski, J. Histochem. Cytochem. (1986) 34:1095–1100.
Huang, et al., J. Lab Invest. (1976) 35:383–390.
Leong, et al., J. Pathology (1988) 156:275–282.
Shi et al., (1991) "Antigen Retrieval in Formalin–fixed, Paraffin–embedded Tissues" The Journal of Histochemistry and Cytochemistry, 39 : 741–478.
Carey et al., (1983) Advanced Organic Chemistry, 2nd ed. 58–62.
Fraenkel–Conrat et al., (1948) "Reaction of Formaldehyde with Proteins (IV)" J. Biol. Chem., 174:827–843.
PCT Search Report dated Oct. 13, 1993.

* cited by examiner

*Primary Examiner*—Mark L Shibuya
*Assistant Examiner*—Shafiqul Haq

(57) ABSTRACT

A method for restoring immunoreactivity of a tissue, particularly decalcified tissue, fixed width an aldehyde fixative agent and embedded in an embedding medium, usually comprising celloidin, the method comprising the steps of contacting the tissue with an aldehyde releasing reagent solution comprising a solvent and an aldehyde releasing reagent and removing aldehyde released by the aldehyde releasing reagent from contact with the tissue by reacting the aldehyde in a substantially irreversible manner to form a non-aldehyde derivative, and removing excess base from the tissue. A preferred solution for celloidin-embedded decalcified tissue comprises methanolic sodium hydroxide at about one-third saturation.

14 Claims, No Drawings

ENHANCEMENT OF IMMUNOCHEMICAL STAINING IN ALDEHYDE-FIXED TISSUE

Matter enclosed in heavy brackets [ ] appears in the original patent but forms no part of this reissue specification; matter printed in italics indicates the additions made by reissue.

RELATED APPLICATION DATA

This application is a continuation-in-part of application Ser. No. 07/928,962, filed Aug. 12, 1992, now abandoned, which in turn is a continuation-in-part of application Ser. No. 07/821,931, filed Jan. 16, 1992, now abandoned.

TECHNICAL FIELD

The invention concerns immunohistochemical staining of aldehyde-fixed and embedded tissue sections.

BACKGROUND

Tissue sections obtained from clinical specimens or animal experimentation frequently are fixed, embedded, and stored in a form suitable for later examination by light microscopy. Immunological reagents, especially monoclonal antibody reagents, currently permit examination of at least certain of these fixed tissue samples for the presence of particular antigenic compounds. Antigens of interest may be associated with a disease process or pathology, or may identify a particular type or tissue. In the case of recently prepared biopsy and autopsy samples, such immunohistochemical analyses are of immediate diagnostic value.

However, immunohistochemical analyses of tissue specimens have been hampered because of antigenic loss during specimen fixation. Traditional fixation methods frequently have employed aldehyde fixatives, which fix the tissue by causing cross-linking reactions within and between tissue proteins.

Two types of cross-linking reactions have been recognized. The first is a Schiff's base-type polymerization: formaldehyde condenses with the amino groups of the protein, resulting in the Schiff's base intermediate, which is capable of undergoing rapid polymerization leading to cross-linking of the proteins.

In the second type of reaction, called the Mannich reaction, the formaldehyde can react with both an amino group and an active hydrogen group, resulting in the formation of a Mannich base. Polymerization of the Mannich bases results in protein cross-linking.

Cross-links preserve tissue morphology and integrity, harden the tissue for slicing, and inhibit microbial attack. Unfortunately, the cross-linking process also causes loss of tissue antigenicity, a result which impedes the usefulness of immunological reagents on tissues fixed with aldehyde reagents such as formaldehyde. The chemistry of the cross-linking of amino acids and proteins by formaldehyde is described in Harlan and Feairheller, "Chemistry of the Cross-Linking of Collagen During Tanning," and Kelly, et al. "Cross-Linking of Amino Acids by Formaldehyde," (1976). The role of Mannich-type reactions in cross-linking of protein amino groups and aromatic amino acids with formaldehyde is discussed in Fraenkel-Conrat, et al., J. Biol. Chem. (1947) 168:99–118, and Fraenkel-Conrat and Olcott, J. Biol. Chem. (1948) 174:827–843. Further discussions of aldehyde cross-linking reactions are found in Fox. J. Histochem. Cytochem. (1985) 33:845–855; Jones, "Reactions of aldehyde with unsaturated fatty acids during histological fixation," in Fixation in Histochemistry, P. J. Stoward, ed. (1973); and Kunkel et al., Mol. Cell. Biochem. (1981) 34:3. Mannich type reactions are described in general in March, "Advanced Organic Chemistry," particularly at 333,424, 670–672 (1968).

In an attempt to circumvent the disadvantages of aldehyde fixation, alternative fixation methods have been developed, such as microwave heating (Mayers, J. Clin. Pathol. (1970) 28:273; Hopwood et al., Histochem. J. (1984) 16:1171) and alcohol immersion (Battiform and Kopinski, J. Histochem. Cytochem. (1986) 34:1095). Despite some advantages of alternative fixation methods, they have not displaced aldehyde fixation in general use. Their limited acceptance may reflect drawbacks present in these alternative methods. For example, microwave heating lyses red cells and disrupts membrane lipids. Although ethanol fixation is reported to produce improved antigenicity of tissue samples, ethanol causes increased cellular shrinkage (Battiform and Kopinski, id.) Consequently methods for restoring antigenicity to aldehyde fixed tissues continue to be useful for specimens generated by current clinical practices.

In addition, methods for restoring antigenicity are useful because of the vast number of aldehyde fixed tissue samples already in collections. These stored tissue samples provide a rich reservoir of material for retrospective immunohistochemical examination. If a suitable method of subsequent immunohistochemical staining were available, newly generated immunohistochemical data could be combined with existing diagnostic results obtained from traditional investigations on the same tissues. Often clinical samples are saved for decades, so that the critical outcome of the patient's underlying pathological process already is known. In the case of experimental tissues, such as those obtained from animals in toxicology testing, other measurements of pathology and toxicity in general already will have been performed and documented. In both cases, immunological analyses of the affected tissues could add important correlative information.

Because of the development of immunological reagents over the past decades, immunohistochemical analyses can now be performed that were impossible at the time many tissues were originally stored. In addition, new knowledge or hypotheses concerning the disease process may prompt reexamination of stored tissues. Immunohistochemical studies on stored tissue samples provide a relatively time- and cost-effective means for performing a clinical study on a statistically large sample population. Therefore the application of immunohistochemical analyses to routine clinically or experimentally derived embedded tissue sections is a matter of considerable interest.

Antigenic loss during aldehyde tissue fixation is due to chemical modification of the protein (not to physical removal of the antigen). Loss of immunoreactivity is believed to occur by two mechanisms. In the first mechanism, the fixative agent chemically modifies the reactive epitope, rendering it incapable of binding antibody. In the second mechanism the fixative agent causes chemical cross-linking of the antigenic protein at sites outside the targeted epitope. Such cross-linking may be intramolecular or intermolecular, i.e., with involvement of nearby proteins. This cross-linking sterically hinders access of the antibody reagent to the reactive epitope.

The second mechanism, steric hindrance due to intraprotein or interprotein cross-linking outside the epitope of interest, has been reversed by protease digestion of formalin fixed tissues in order to remove the interfering cross-linked portions of proteins. This approach has been shown to improve immunostaining of keratins in formaldehyde fixed tissues (Battifora and Kopinski, J. Histochem. Cytochem. (1986) 34:1095–1100). However, protease treatment actually degraded the staining of tissues fixed in alcohol, a fixative solution which does not cause protein cross-linking. Some improvement in immunostaining by proteolysis of formaldehyde fixed tissues for limited time periods has been shown for other antigens (Huang, et al., J. Lab Invest. (1976) 35:383–390.) In a study of immunostaining of 23 antigens of pathological interest, prior trypsinization was shown to give no improvement in immunostaining of formaldehyde fixed tissues except in the case of cytokeratins and desmin. For many antigens, enzyme digestion actually diminished antigen staining. (Leong, et al., J. Pathology (1988) 156:275–282.) These results support the hypothesis that aldehyde fixative-induced cross-linking of proteins diminishes immunostaining both by chemical modification of epitopes and by steric hindrance mediated by cross-linking. The mixed results obtained from treating fixed tissues with proteolytic enzymes are readily rationalized: although partial proteolysis decreases cross-linking and reduces steric hindrance, proteolysis also may cleave and remove the epitopes of interest. Moreover, proteolysis cannot reverse antigenic masking due to chemical modification of the epitope. By contrast, a procedure which could reverse the chemical cross-linking reaction produced by aldehyde fixatives has the potential to unmask antigens previously hidden by either mechanism.

A procedure for restoring antigenicity of formalin-fixed, paraffin embedded tissue sections by heating the tissue in a microwave in a heavy metal solution has been described in Shi, et al. J. Histochemistry and Cytochemistry 39(b): 741–48 (1991). This procedure provides enhanced immunostaining in approximately three-fourths of the samples tested. The described methods is part of a process that involves the steps of tissue section deparaffinization and rehydration, brief treatment with aqueous peroxide to block endogenous peroxidase, washing of the slides with distilled water, coveting the slides with distilled water or a heavy metal solution, and brief microwave heating for several minutes. Following this procedure, slides are cooled, rinsed, and immunostained in a conventional fashion.

This method for restoring antigenicity is subject to certain limitations. First, it requires the use of a microwave oven to heat the tissue samples. Many laboratories may not be equipped with a microwave oven, and some tissue samples may not be suited to microwave heating. A need exists for an antigen retrieval method that can be used at room temperature, without any external heat source. In addition, the previously described procedure is especially suitable for tissues embedded in a hydrocarbon medium such as paraffin. It is not well suited for tissue sections embedded in celloidin, a preferred embedding medium for bony tissues. A need also exists for a method which is suitable for use with celloidin embedded tissues. Moreover, a need particularly exists for a method which may be used with decalcified bony tissue samples, since decalcified tissues are often refractory to the previously described method.

Methods and compositions are provided for restoring antigenicity for immunohistochemical analysis of aldehyde fixed tissue. The methods and compositions are especially useful with celloidin embedded tissue and with decalcified bony tissue. The method involves treating aldehyde fixed tissue with a chemical agent or agents that catalyze an essentially irreversible Mannich/Schiff's Base reaction which converts the aldehyde released thereby into a nonreactive form, i.e., into a non-aldehyde derivative. In this application such chemical agent or agents will be termed an "aldehyde releasing agent." In one aspect, the aldehyde releasing reagent comprises a nucleophilic reagent solution and the method involves. (1) treating aldehyde fixed tissue with the nucleophilic reagent solution, optionally containing a chaotropic agent, (2) removing excess nucleophile by neutralizing or rinsing the tissue sample, and (3) reacting the tissue with an immunoreactive agent. In another aspect, the aldehyde releasing reagent comprises an oxidizing agent and the method involves (1) treating aldehyde fixed tissue with the oxidizing agent, (2) removing excess agent and (3) reacting the tissue with an immunoreactive reagent. In a third aspect, the aldehyde releasing reagent comprises an organic acid/base pair and the method in step (1) involves treatment with the organic acid/base pair. Exemplary organic acids are set forth below. Exemplary bases are sodium hydroxide and potassium hydroxide. Also provided is a kit for immunostaining of aldehyde fixed tissue. The kit minimally comprises a solution for restoring antigenicity comprising a solvent and an aldehyde releasing reagent. Optionally, the kit can also comprise a solution to remove excess aldehyde releasing reagent or a reagent immunostaining reagent.

The invention provides a method for restoring immuoreactivity of a tissue fixed with an aldehyde fixative agent and embedded in an embedding medium, the method comprising the initial step of contacting the tissue with an solution for restoring antigenicity comprising a solvent and an aldehyde releasing reagent. The aldehyde releasing reagent catalyzes reversal of the reaction between the aldehyde and biological components in the tissue, such as by catalyzing a reverse Mannich or a reverse Schiff base reaction. The released aldehyde reacts in a substantially irreversible manner to form a non-aldehyde derivative. Alternatively, the initial step can be broken down into two steps by adding the components of the antigenicity restoring solution separately: fist adding solvent to remove at least part of the embedding medium, followed by adding an aldehyde releasing reagent, usually in the same or a different solvent. The initial step is followed by removing excess aldehyde releasing reagent from the tissue prior to immunostaining. Preferred embodiments of the invention provide a method for restoring immunoreactivity of a decalcified tissue fixed with an aldehyde fixative agent and embedded in an embedding medium comprising celloidin. Specific embodiments are described in complete detail below. A general theory of how the invention operates is set forth immediately below, along with a brief discussion of the physical and chemical processes that are believed to take place during the initial fixation process and the antigenicity restoring process of the invention. It must be understood that these are merely theories, and the invention can be fully practiced simply by reference to the descriptions of specific operations (and variations thereof) to be carried out by the practitioner.

The aldehyde fixation of tissue is believed to produce cross-linked proteins. This cross-linking is mediated by the reaction of aldehyde groups in the fixative with amino groups on amino acid residues of tissue proteins, such as lysine and the N-terminal a-amino acid group. The initial product of this interaction is an amino-aldehyde conjugate, either an imino Schiff base ($CHR_1{=}NR_2R_3$) or an aminomethylo ($CHR_1OHNR_2R_3$) intermediate. The intermediate may then undergo nucleophilic attack by susceptible neighboring amino acid groups, such as $\alpha$-carbonyl methylene carbons having an acidic proton, nucleophilic heteroatoms, or electron rich aromatic rings. Prime nucleophiles include aromatic rings such as the ortho-position of the phenol ring of tyrosine, the C-2 position of the indole ring of tryptophan, and the imidazole ring of histidine; the a-carons adjacent to the side chain carboxylic acid groups of glutamate and asparatate; basic heteroatoms such as lysyl ϵ-amino groups; and neutral nitrogen atoms such as asparaginyl and glutaminyl amide groups and the indole ring nitrogen of tryptophan. Formally, all such reactions are types of or at least similar to Mannich reactions, at least inasmuch as the reactive electrophile is the intermediate amino-aldehyde conjugate species. These reactions result in a covalent bond between the electrophilic aldehyde carbon and a nucleophilic carbon or heteroatom.

The resulting cross-linking fixes proteins in a particular conformation and fixes the entire tissue by forming covalent bonds among adjacent proteins. The cross-linked proteins resist penetration by macromolecules such as antibodies. In addition, chemical modification or epitopes (which contain amine, amide, or aromatic amino acid residues) produces an altered structure unrecognizable to an antibody against that epitope.

The commonest aldehyde fixative is formaldehyde, which is unifunctional and produces cross-linking by direct contact between methylol-amino groups of lysine and adjacent susceptible amino acid target residues. However, other difunctional or polyfunctional cross-linking aldehydes are known. Of these the commonest is glutaraldehyde, a five carbon chain with aldehyde at both termini. This difunctional reagent provides additional opportunities for cross-linking, since the alkyl chain of the reagent functions as a spacer. The mechanism of reaction is believed similar, regardless of the particular aldehyde reagent used for fixation.

The method of the present invention provides a means for reversing or breaking at least some of these cross-linkages, thereby restoring the antigenicity of previously fixed proteins. The method involves treating the previously aldehyde-fixed tissue with a solution containing an aldehyde releasing reagent, which is believed to promote reversal of the Mannich-type reaction and other reactions between formaldehyde and tissue components. Antigenic restoration also may proceed as a result of limited proteolysis. In order to effectively restore antigenicity, the reagent need not reverse or break all aldehyde induced linkages. Partial breakage of cross-linkings loosens the fixed proteins sufficiently to permit penetration by antibodies. Particularly susceptible linkages are believed to be those produced between aminomethylol reactants and heteroatoms, such as amines and amides, or alpha-carbonyl methylene groups.

Most effective aldehyde releasing reagents for the practice of the invention are nucleophiles, preferably basic nucleophiles. An especially preferred nucleophile is hydroxide anion, which is conveniently supplied as an alkali metal hydroxide such as sodium or potassium hydroxide. Other convenient nucleophiles include primary, secondary, or tertiary amines, especially those with minimal steric hindrance to attack, such as piperidine or morpholine. Hydroxylamine and glycine are preferred. Other nucleophiles include thiols such as mercaptoethanol. Yet another nucleophile of interest is azide, e.g. sodium azide ($NaN_3$). In general, any nucleophile capable of promoting a reverse Mannich reaction will be capable of cleaving at last some protein cross-linkings, as such reagents will also catalyze reversal of other types of reactions caused by formaldehyde. The concentration of the nucleophile may vary widely, with more concentrated solutions acting more quickly. For short exposures, nucleophile concentrations of 0.5M or greater are usually preferred. In the case of NaOH in methanol, concentration of one-tenth to one-half of saturation (approximately 0.6 to 3M) are preferred in most circumstances. For hydroxylamine, for example in the form of hydroxylamine hydrochloride, or for glycine, a 10% aqueous solution is preferred. Additional nucleophiles include hydrazine hydrate. And for hydrazine hydrate, an aqueous (v/v) solution in the range of about 2.0% to about 5.0% preferably 5.0%, is suitable.

Other effective aldehyde releasing reagents for the practice of the invention are oxidizing agents. Preferred oxidizing agents are hydrochlorites and periodates, especially sodium hydrochlorite or sodium periodate. Concentration of the oxidizing agent will vary with the reagent. For example, for sodium hypochlorite, an aqueous (v/v) solution in the range of about 0.01% to about 0.005%, preferably 0.005%, is suitable. For sodium periodate, an aqueous (v/v) solution in the range of about 0.1% to about 1.0%, preferably 0.1%, is suitable. Treating the sample with the oxidizing agent is believed to break the cross-linkages between the aldehyde and tissue components and converts the released aldehyde into a non-reactive form, for example by converting formaldehyde to formic acid.

We have found that certain acid/base pairs will function as an aldehyde releasing releasing agent within the confines of this invention. The following pairs are exemplary:

| Organic Acid/Base Pair (Acid/Base) | Concentration (Acid/Base) | Minutes |
|---|---|---|
| Trichloroacetic Acid/NaOH | 10% aqueous/10% NaOH in methanol | 10/20 |
| Toluene Sulfonic Acid/NaOH | 5% aqueous/40% aqueous | 30/30 |
| Citric Acid/NaOH | 10% aqueous/40% aqueous | 30/30 |
| Oxalic Acid/NaOH | 20% aqueous/40% aqueous | 30/30 |
| Tartaric acid/NaOH | 10% aqueous/40% aqueous | 30/30 |

The solvent for the aldehyde releasing reagent solution may be any solvent compatible with and capable of dissolving the aldehyde releasing reagent. Aqueous solutions are possible; and preferable where the aldehyde releasing reagent is an oxidizing agent or an organic acid/base pair. Organic solutions are preferable where the aldehyde releasing reagent is a nucleophile because they promote better penetration of the embedding medium. In addition, proteolytic fragments are insoluble in most organic solvents and therefore tend to remain in place on the slide.

A preferred solvent for use with celloidin embedded tissue sections is a polar organic solvent. Alcoholic solutions are preferred because they promote good penetration of the celloidin embedding medium and are good solvents for nucleophiles of interest, especially alkaline metal hydroxides. Lower alcohols are preferred, such is methanol, ethanol, propanol, and butanol; methanol is especially preferred. Polyols such as ethylene glycol and glycerol are also useful; they have the advantages of low volatility and greater viscosity, which permit them to remain on the slide for an extended period without evaporating or running off. Polar aprotic solvents such as dimethyl formamide (DMF) and dimethyl sulfoxide (DMSO) also may be used with appropriate nucleophiles. Furthermore, mixed solvent solutions are acceptable, provided the component solvents are compatible with the reagents and each other.

Two solvents may be used consecutively under some circumstances. For example, a celloidin embedded slide may be treated initially with methanol to solubilized the embedding medium, then treated with an aldehyde releasing reagent solution such as KOH in glycerol.

Nonpolar organic solvents are useful with tissues embedded in nonpolar media such as paraffin. In the case of a nonpolar solvent such as toluene, a quaternary base is desirable since it is soluble in nonpolar solvents. Examples include tetraalkylammonium hydroxide (e.g. tetraethylammonium hydroxide) or a quaternary phosphonium salt. A nonpolar solvent and quaternary base may be combined with an immiscible polar aqueous phase in a phase-transfer reaction. The two phases may be applied to the tissue simultaneously, or the nonpolar phase may be applied first in order to facilitate solubilization of the paraffin embedding medium.

Additives may be included to enhance the desirable properties of the solution. Chaotropic agents, such as sodium thiocyanate, are preferred additives.

The embedded and fixed tissue sections are immersed in or covered by the aldehyde releasing reagent solution for periods ranging from several minutes to several hours. The optimal treatment period will vary depending concentration of aldehyde releasing reagents, type of solvent (if any), degree of penetration of the embedding medium by the solution, extent of tissue fixation, and temperature. For a particular combination of variables, an optimum time of treatment may be readily determined by treating tissue samples for different increments of time and measuring the extent of immunostaining. For a solution comprising methanolic sodium hydroxide at 25% saturation, a period of treatment of about 30 minutes is adequate for most tissue sections. Little improvement is seen for times less than about 5 minutes. At periods of contact longer than about 2 hours, the tissue may tend to detach from the slide; this is especially pronounced with 20 mm celloidin sections.

The treatment temperature affects reaction rate in the typical predictable pattern for chemical reactions, with elevated temperatures producing more rapid results. The method may be practiced conveniently at room temperature, and temperature control is not normally practiced.

After the treatment period with the aldehyde releasing reagent solution, excess reagent is removed from the tissue sample prior to immunostaining. This may be accomplished most conveniently by rinsing the tissue with solvent or solution which is free of the reagent. Multiple changes of rinsing solution are preferred. For greater preservation of tissue hydration and morphology characteristics, at least one of the rinsing solution preferably will contain a mixture of the solvent used in the aldehyde releasing reagent solution and aqueous buffer. This facilitates re-equilibration of tissue with buffer. Preferably one or more washes with aqueous buffer will be performed prior to immunostaining. A preferred rinsing procedure uses at least one wash with buffer containing a detergent follows by one or more rinses with buffer containing a detergent followed by one or more rinses with buffer without detergent. The detergent may be any tissue compatible detergent, either ionic or non-ionic, although non-ionic detergents such as Triton X-100 are preferred.

As an alternative to the rinsing step, excess reagent may be neutralized with acid or a buffer. This alternative is most feasible when the solvent is similar or identical in composition to the solution to be used for the immunostaining. In general, immunostaining solutions are themselves aqueous buffers. For most applications, removal of excess base by rinsing will be preferable.

After removal of excess reagent, the tissue is immunostained by any conventional technique. A great variety of immunostaining procedures, reagents, and antibodies are known, many of which are commercially available. The procedures for restoring antigenicity described above leaves the tissue in a condition compatible with most immunostaining procedures. Typically, the tissue is incubated with a primary antibody against the antigen of interest, followed by treatment with a detectable label. The detectable label often includes a second antibody against the primary antibody; in turn, the second antibody may have the capacity to bind with a third species which is actually detected. These multiple levels of binding provide a means for amplifying the intensity of the detectable signal. In general, the antigen retrieval method described above does not interfere with the detection procedure.

The present method for restoring antigenicity using aldehyde releasing reagents may be used with essentially any embedding medium, including hydrocarbons, such as paraffin, and synthetic resins. However, it is particularly useful with celloidin, which is a traditional embedding medium for bony tissues. Celloidin is a pure form of pyroxylin, the low-nitrogen form of nitrocellulose. Celloidin is available from various commercial sources.

The described method preferably is performed with solution which either solubilizes or swells and softens the embedding medium. Most embedding media are supplied as solutions. Hence an appropriate solvent for the solution may be inferred based upon the solvation characteristics (e.g. hydrophobicity, polarity, hydrogen bond donor/acceptor potential) of the solvent supplied for the embedding medium. The solution need not employ a solvent identical to that used for the embedding medium. However, the identity of suitable embedding medium solvents provides a guideline to the appropriate characteristics for the aldehyde releasing solvent.

In the case of celloidin, the embedding medium is soluble in ether-alcohol mixtures, clove oil (comprising aromatic terpenes), alcohols, and acetone. Methanol is a suitable solvent, since it also solubilizes basic nucleophiles, and is a preferred solvent for use with celloidin embedded tissues.

Bony tissues in the past have presented particular problems, at least in part because of the decalcification treatment to which bone often is exposed during fixation. Conventional decalcification is performed with an acid such as trichloroacetic acid ($Cl_3CCOOH$). At present, immunohistochemical staining is not widely in diagnostic and investigative pathology for routinely processed formaldehyde fixed, decalcified, and celloidin embedded bony tissues, as for example temporal bone sections. Several reported attempts to immunostain temporal bone sections focus on modified fixation, decalcification, and embedding protocols (Veldman et al., Advances in oto-immunology. New trends in functional pathology of the temporal bone, Laryngoscop (1987) 97:413; Huizing et al., Progress in temporal bone histopathology. I. Semithin 3–5 um sectioning of undecalcified human temporal bone after plastic embedding, Acta Otolaryngol (Stockh) (1985) Suppl 423:24; Veldman et al., Progress in temporal bone histopathology, II. Immunotechnology applied to the temporal bond, Acta Otolaryngol (Stockh) (1985) Suppl 423:29; Arnold, W., Immunohistochemical investigation of the human inner ear, Acta Otolaryngol (Stockh) (1988) 105:392; and Bauwens et al., Progress in temporal bone histopathology. III. An improved technique for immunohistochemical investigation of the adult human inner ear, Acta Otolaryngol (Stockh) (1990) Suppl 470:34).

The disclosed method simultaneously neutralizes any residual acidity from decalcification, which might impede restoration of antigenicity using water or other solvent by itself with bony specimens. As the accompanying experimental results demonstrate, the disclosed method permits effective immunostaining of temporal bone sections which have been routinely processed and embedded. This is significant because human temporal bone collection amounting to 8,000 and 13,000 specimens exist in Europe and the United States, respectively (Schuknecht, Ann. Otol. Rhinol. Laryngol, (1987) 96 (Suppl. 130):1). These collections provide an excellent research base for understanding otopathology by light microscopy.

A kit for use in immunostaining of a tissue can be provided to simplify practice of the method described above. The kit will minimally contain a receptacle adapted to hold one or more individual reagent containers and at least a first container containing (1) an aldehyde releasing reagent solution comprises a solvent and an aldehyde releasing reagent or (2) the aldehyde releasing reagent in an amount appropriate to make up the desired concentration when solvent from another container is used to fill the aldehyde releasing reagent container to a predetermined level. In most cases, the kit will also contain a second container containing (1) an immunostaining reagent or (2) a wash solution for removing excess aldehyde releasing reagent solution, or containers with both such material. Wash solutions are typically buffered solutions that do not further dissolve or swell the embedding medium, such as aqueous buffered solutions. The solvent in the wash solution will be capable of dissolving the solvent and aldehyde releasing reagent used in the antigen retrieval alcohol. The immunostaining reagent generally comprises an antibody and staining moiety. Such reagents are well known in the art and require no further description here. Specific examples are given in the general examples of the invention set out below. Appropriate instructions for carrying out the method of the invention will also be included in the kit.

The invention now being generally described, the same will be better understood by reference to the following detailed examples which are provided for illustration and are not to be considered as limiting the invention unless so specified.

EXAMPLE 1

A Nucleophile as an Aldehyde Releasing Reagent

1. Materials and Methods

A total of 60 celloidin-embedded human temporal bone sections were obtained from the Eastern National Temporal Bone Bank at Massachusetts Eye and Ear Infirmary (Table 1). Most sections were processed routinely by either Heidenhain-Susa or 100% formalin fixation and decalcified by 5% trichloracetic acid as described previously (Schuknecht HF. Pathology of the Ear. Cambridge, Mass.: Harvard University Press, 1974). Only one case was processed by a modified method using 10% neutral buffered formalin fixative and EDTA decalcification.

The monoclonal antibodies used are listed in Table 2. All antibodies were obtained from BioGenex Laboratories (San Ramon, Calif.). Most slides were stained with Super Sensitive biotin-streptavidin kits (SSBSA) from BioGenex. A few slides were stated by ABC kits purchased from Vector Laboratories, Inc. (Burlingame, Calif.).

b 2.Preparation of Aldehyde Releasing Reagent Solution

Sodium hydroxide (NaOH) in methanol solution provides one formulation of the basic reagent used in these experiments. NaOH, 50–100 grams, was added to 500 ml methanol in a brown colored bottle. The solution was mixed by shaking and stored at room temperature for 1–2 weeks to settle. The upper layer of liquid was removed carefully from the precipitate, and diluted 1:3 in methanol. Prior to use, 0.01% sodium thiocyanate optionally was added.

3. Treatment of Tissue Sections

The celloidin-embedded temporal bone sections were washed in distilled water for 10 minutes, mounted on 0.1% poly-L-lysine (Sigma) coated slides. The slides were immersed in one-quarter saturated NaOH-methanol solution (saturated methanolic NaOH, approximately 6M, diluted 1:3 with methanol) alone or with added 0.01% sodium thiocyanate, for 30 minutes. Slides were rinsed for 15 minutes in two changes of 100% and 70% methanol and two changes of phosphate buffer saline (PBS), followed by treatment with 0.3% Triton X-100 for 10 minutes and rinsing in PBS again.

4. Immunostaining Procedures

Treatment was followed by a three-step immunostaining technique using either the SSBSA or the ABC method, as previously described (Shi et al., J. Histochem. Cytochem. (1991) 39:741). Briefly, slides were incubated with primary antibody overnight at room temperature followed by a 40 to 60 minute incubation with link (BioGenex Super Sensitive biotinylated anti-mouse immunoglobulin or Vector biotinylated anti-mouse immunoglobulin). Label (BioGenex Super Sensitive Alkaline phosphatase conjugated streptavidin or peroxidase conjugated streptavidin and Vector ABC) was added for 40 to 60 minutes. Slides were rinsed between incubation in three changes of PBS for 15 minutes. Either fast red or DAB chromgen was used as substrate. The immunostaining results were controlled by light microscopy.

The primary antibody was replaced with either nonspecific mouse ascites or PBS for negative control slides.

TABLE 1

Routine celloidin-embedded human temporal bone sections used (N = 60)

| Code | No. of sections | Fixation | Decalcification | Cut | Stored |
|---|---|---|---|---|---|
| P.F. | 10 (L&R) | NBF | EDTA | Recent | <1 yr |
| C.B. | 10 (R) | H-S | TCA | 1989 | <2 yrs |
| R.L. | 10 (L) | F | EDTA | 1989 | <2 yrs |
| G.H. | 10 (R) | H-S | TCA | 1986 | 4 yrs |
| J.P. | 10 (R) | H-S | TCA | 1982 | 8 yrs |
| R.Y. | 10 (L) | F | TCA | 1960 | 30 yrs |

a. L = left side, R = right side of temporal bone.
b. NBF = 10% neutral buffered formalin, H-S = Heidenhain-Suxa fixative, F = 10% formalin.
c. TCA = trichloroacetic acid.

5. Results

The immunoreactivity of 15 monoclonal antibodies used on routinely processed celloidin-embedded sections is summarized in Table 2. The staining results showed strong positive staining for 7 monoclonal antibodies, moderate positive staining for four antibodies, and weak positive staining for one antibody. Three antibodies showed negative results. There was no significant difference in immunoreactivity between various sections. All negative control slides (PBS or nonspecific mouse ascites) showed negative staining. The intensity of immunostaining obtained by the SSBSA system was stronger than that obtained by the ABC system.

The immunoreactivity of monoclonal antibody to kernfin (AEI and NCL-5D3), vimentin, neurofilament, muscle specific actin, S-100 protein, neuron specific enolase (NSE), glial fibrillary acidic protein (GFAP) and others showed strong positive results. In a routine celloidin embedded human temporal bone section that was immunostained with monoclonal anti-keratin antibodies NCL-5D3 and AE1 following treatment with aldehyde releasing reagent, all epithelial cells lining the coacher duct were distinctly labeled by the anti-keratin antibodies. Keratin localization within the organ of Corti was also discernible. The keratin immunoreactivity showed so distinctively that all epithelial cells were precisely demonstrated by the immunohistochemical staining.

Other celloidin embedded temporal bone sections immunostained with monoclonal antibodies after treatment with aldehyde releasing reagent solution also showed strong positive results. Antibody against neuron specific enolase (NSE) was localized in spiral ganglion neurons and neurofibers. Anti-NSE immunostaining was localized within inner hair cells in the organ of Corti but was absent in outer hair cells except at the bottom of the outer hair cells where it occurred possibly in synapses and terminal nerve branches. Glial fibrillary acidic protein (GFAP) was localized along the glial-Schwann junction to the brain side only. Desmin was localized in tensor tympanic muscle by anti-desmin antibody. This labeling with anti-desmin antibody was not possible using micro-dissection methods (Bauwens et al., Acta Otolaryngol. (1990) Suppl. 470:34). The skin and appendages of dermis in the external auditory canal were also stained positively by some antibodies such as keratin and actin. Tubulin was widely localized in most epithelial and mesenchymal cells of whole temporal bone.

TABLE 2

Immunohistochemical Staining on Routine Processed, Celloidin-Embedded Human Temporal Bone Sections

| Monoclonal Antibody | Results |
|---|---|
| Keratin: | |
| AE1 | +++ |
| NCL-5D3 | +++ |
| Vimentin | +++ |
| NF | +++ |
| GFAP | +++ |
| Desmin | ++ |
| Myoglobin | ++ |
| n-Tubulin | ++ |
| b-Tubulin | + |
| Muscle Specific Actin | +++ |
| Chromogranin | – |
| n-Actinin | – |
| EMA | – |
| NSE | ++ |
| S-100 | +++ |

Immunoreactivity was scored on a scale of – to +++, – being non-reactive and +++ being highly reactive.

EXAMPLE 2

An Oxidizing Agent as an Aldehyde Releasing Reagent

1. Preparation of Solution

Sodium hypochlorite (NaClO) in distilled water solution provides one formulation of the basic reagent used in these experiments. NaClO, 0.01–0.005 grams, was added to 100 ml of distilled water in a brown colored bottle. The solution was mixed by shaking and storing at room temperature.

2. Treatment of Tissue Sections

The deparaffinized tissue slides were washed in distilled water for 10 minutes. The slides were immersed in an aldehyde releasing reagent solution, i.e., dilute sodium perchlorate (aqueous) solution for 10 minutes.

3. Immunostaining Procedures and Results

Treatment was followed by a three-step immunostaining technique. Briefly, slides were incubated with primary antibody overnight at room temperature followed by a 20–30 minute incubation with a link (BioGenex Super Sensitive biotinylated anti-mouse immunoglobulin or Vector biotinylated anti-mouse immunoglobulin). A label (BioGenex Super Sensitive Alkaline phosphatase conjugated streptavidin or peroxidase conjugated streptavidin and Vector ABC) was added for 20–30 minutes. Between incubation, slides were rinsed in three changes of PBS for 15 minutes. Either fast red or DAB chromogen was used as a substrate. The immunostaining results were controlled by light microscopy. Positive results were seen.

EXAMPLE 3

An Organic Acid/Base Pair as an Aldehyde Release Reagent

The deparaffinized tissue slides were washed in distilled water for 10 minutes. The slides were loaded with a 5–10% aqueous solution of a citric acid. After waiting for 10–30 minutes, the slides were loaded with a 10% methanolic/aqueous solution of sodium hydroxide (prepared as set forth in Example 1) for 10–30 minutes. Immunostaining proceeded as set forth in Example 2 and positive results were seen.

The invention now being fully described, it will be apparent to one of ordinary skill in the art that many changes and modifications can be made thereto without departing from the spirit or scope of the appended claims.

We claim:

1. A method for restoring immunoreactivity of a tissue fixed with an aldehyde fixing agent and embedded in an embedding medium, said method comprising the steps of:

a) contacting said tissue with a solvent for said embedding medium and an aldehyde releasing reagent, which reagent releases aldehyde from said tissue by reacting said aldehyde in a substantially irreversible manner to form a non-aldehyde derivative; and b) removing or neutralizing excess aldehyde releasing reagent from said tissue.

2. The method of claim 1, wherein said solvent is selected from the group consisting of methanol, ethanol, propanol, butanol, ethylene glycol, and glycerol.

[3. The method of claim 1, wherein said aldehyde releasing reagent is selected from the group consisting of nucleophilic bases, oxidizing agents and organic acid/base pairs.]

[4. The method of claim 1, wherein said aldehyde releasing reagent is an oxidizing agent.]

[5. The method of claim 1, wherein said aldehyde releasing reagent is a nucleophilic base.]

6. The method of claim 1, additionally comprising in step a) contacting said tissue with a chaotropic agent.

7. The method of claim 1, wherein said tissue comprises decalcified tissue.

[8. A kit for use in immunostaining of a tissue fixed with an aldehyde fixing agent and embedded in an embedding medium, said kit comprising:

a) a first container containing an aldehyde releasing reagent solution comprising an aldehyde releasing reagent selected from the group consisting of nucleophilic bases, oxidizing agents and organic acid/base pairs and a solvent for the aldehyde releasing reagent which is also capable of solubilizing the embedding medium; and b) a second container containing (1) an immunostaining reagent or (2) a wash solution for removing excess aldehyde releasing reagent.]

9. The method of claim *1* [3] wherein said *solvent* [aldehyde releasing reagent] is an aqueous or organic solution.

[10. A kit for use in immunostaining of a tissue fixed with an aldehyde fixing agent and embedded in an embedding medium, said kit comprising:

a) a first container containing an aldehyde releasing reagent selected from the group consisting of nucleophilic bases, oxidizing agents and organic acid/base pairs;

b) a second container containing a solvent for solubilizing the embedding medium; and c) a third container containing (1) an immunostaining reagent or (2) a wash solution for removing excess aldehyde releasing agents.]

[11. The kit of claim 8 or 10 wherein said aldehyde releasing reagent comprises a nucleophilic base.]

[12. The kit of claim 8 or 10 wherein said aldehyde releasing reagent comprises an oxidizing agent.]

[13. The kit of claim 8 or 10 wherein said aldehyde releasing reagent comprises an organic acid/base pair.]

[14. The kit of claim 8 or 10 wherein said solvent is selected from the group consisting of methanol, ethanol, propanol, butanol, ethylene glycol, and glycerol.]

[15. The kit of claim 8 or 10 wherein said second container contains an immunostaining reagent comprising an antibody.]

*16. A method for restoring immunoreactivity of a tissue fixed with an aldehyde fixing agent and embedded in an embedding medium, said method comprising the steps of:*

*a) contacting said tissue with a solvent for said embedding medium and an organic acid/base pair aldehyde releasing reagent, which reagent releases aldehyde from said tissue by reacting said aldehyde in a substantially irreversible manner to form a non-aldehyde derivative; and*

*b) removing or neutralizing excess aldehyde releasing reagent from said tissue.*

*17. The method of claim 16, wherein said solvent is selected from the group consisting of methanol, ethanol, propanol, butanol, ethylene glycol, and glycerol.*

*18. The method of claim 16, additionally comprising in step a) contacting said tissue with a chaotropic agent.*

*19. The method of claim 16, wherein said tissue comprises decalcified tissue.*

*20. A method for restoring immunoreactivity of a tissue fixed with an aldehyde fixing agent and embedded in an embedding medium, said method comprising the steps of:*

*contacting the tissue with a solvent for the embedding medium and an oxidizing reagent, wherein the reagent releases aldehyde from the tissue by reacting the aldehyde in a substantially irreversible manner to form a non-aldehyde derivative; and*

*removing or neutralizing excess reagent from the tissue.*

*21. The method of claim 20, wherein the solvent is selected from the group consisting of: methanol, ethanol, propanol, butanol, ethylene glycol, and glycerol.*

*22. The method of claim 20, further comprising contacting the tissue with a chaotropic agent.*

*23. The method of claim 20, wherein the tissue comprises decalcified tissue.*

*24. The method of claim 20, wherein the solvent is an aqueous or organic solution.*

* * * * *